Figure 1:
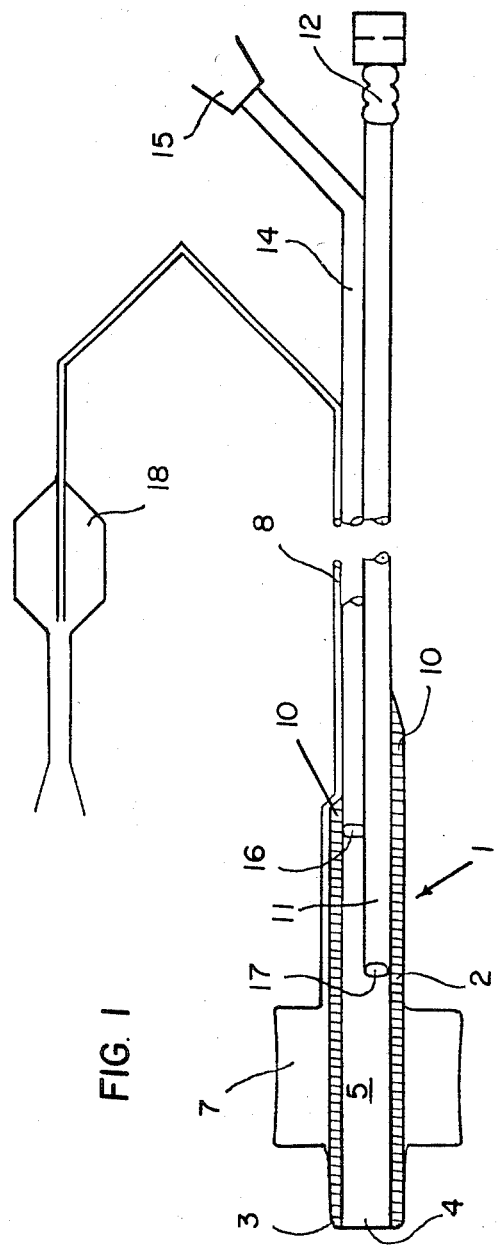

United States Patent [19]

Weerda et al.

[11] Patent Number: 4,565,194
[45] Date of Patent: Jan. 21, 1986

[54] TRACHEAL TUBE FOR ARTIFICIAL RESPIRATION

[75] Inventors: Hilko Weerda, Bad Krozingen; Gerhard Meuret; Peter Pedersen, both of Freiburg, all of Fed. Rep. of Germany

[73] Assignee: Drägerwerk AG, Fed. Rep. of Germany

[21] Appl. No.: 538,416

[22] Filed: Oct. 3, 1983

[30] Foreign Application Priority Data

Feb. 6, 1982 [DE] Fed. Rep. of Germany ....... 3204110

[51] Int. Cl.⁴ .............................................. A61M 16/00
[52] U.S. Cl. ........................... 128/204.23; 128/204.25; 128/205.19; 128/207.15
[58] Field of Search ....................... 128/204.25, 207.15, 128/205.19, 911, 204.23, 204.21, 204.24

[56] References Cited

U.S. PATENT DOCUMENTS

| 4,265,237 | 5/1981 | Schwanbom et al. | 128/204.25 |
| 4,270,530 | 6/1981 | Baum et al. | 128/204.25 |
| 4,289,128 | 9/1981 | Rusch | 128/204.25 |

FOREIGN PATENT DOCUMENTS

| WO82/03014 | 9/1982 | PCT Int'l Appl. | 128/207.15 |
| 2063686 | 6/1981 | United Kingdom | 128/204.25 |

Primary Examiner—Henry J. Recla
Attorney, Agent, or Firm—McGlew and Tuttle

[57] ABSTRACT

A tracheal tube (1) for giving artificial respiration to a patient comprises a balloon cuff (7) for sealing. The respiration gas is blown in by producing excess pressure, and taken off by producing underpressure, in a respiration tube (11) having a relatively small diameter. To monitor the intratracheal pressure in the closed respiratory system, a pressure measuring cannula (14) is provided, so that a respiration within the desired intratracheal pressure range can be ensured, through an electronic control device (29), by a respirator (13) operating to blow in an exhaust respiratory gas.

13 Claims, 2 Drawing Figures

TRACHEAL TUBE FOR ARTIFICIAL RESPIRATION

The invention relates to a tracheal tube for giving artificial respiration to a patient, particularly in endolaryngeal surgery, comprising a balloon cuff by which the tracheal tube open at its end to be introduced is surrounded and which is connected to an inflating cannula, and a flexible respiration tube for injection ventilation, terminating in the tracheal tube.

For direct laryngoscopy and endolaryngeal surgery, two different methods of artificial respiration are known. In the first method, the ventilation is effected through a tube having a relatively large diameter (28 French=9.3 mm of outer diameter) and being fixed in place in the trachea by means of a so-called cuff or balloon cuff so that the anesthetist can securely maintain the respiration. However, to the laryncologist, such a tube obstructs the view of the posterial larynx, since the diameter of the tube is relatively large.

Aside from this respiration in a closed system, the open injection ventilation is also employed by anesthetists in the laryngoscopy, which is an open system including an extralaryngeal injection cannula secured to the operating laryngoscope. In one variant of this second method of respiration, the injection ventilation is produced by means of an intratracheal sound or of a locally fixed tube which is open to the carina and the larynx (modified carden tube, model Ulmer). With such a short intratracheal tube having an injection sound welded therein, however, the optimum sight is paid for by a lack of security in the respiration. As in every open system of respiration, there is a danger of aspiration and, in addition, no possibility of an accurate clinical monitoring of the respiration. This leads to hypoventilation and also hyperventilation. Particularly patients with a small lungs compliance are not always satisfactorily ventilated with such respiration systems.

Starting from this prior art, the invention is directed to a tracheal tube of the above mentioned kind, having the advantages both of a secure ventilation of a closed respiratory system and of the optimum sight inherent in the known open systems of respiration.

To this end and in accordance with the invention, it is provided that the tracheal tube is closed at its distal end turned to the respiration tube, and that a pressure measuring cannula projects into the interior of the tracheal tube.

By means of the pressure measuring cannula, the intratracheal pressure can be monitored and limited upwardly and downwardly by means of an electronic control in the connected respirator. In this way, a suction part is added to the injection part, and a closed injection ventilation is made possible.

While in prior art injection ventilation, the respiration tube is employed only for blowing breathing gas in, the inventive respiration tube of the tracheal tube can also be used for aspiration, while the intratracheal pressure is controlled through the pressure measuring cannula in a way such as to avoid any occurrence of excess pressure or low pressure which might endanger the lungs of the patient. Measuring of the intratracheal pressure makes it possible to compensate for the pressure drop in the respiration tube where the resistance to flow is so strong that the compliance of the lungs at exhalation is not sufficient for overcoming this resistance to flow without external help.

In an advantageous embodiment, the respiration tube, the pressure measuring cannula, and the inflating cannula are welded to each other at the distal end of the tracheal tube and also over a predetermined length, so that a flexible bundle of tubes is formed requiring little space.

It is advisable to let the respiration tube project into the tracheal tube farther than the pressure measuring cannula.

In a respirator to be connected to the inventive tracheal tube, a control equipment is provided operating to produce excess pressure during the inspiration phase and lower pressure during the expiration phase in the respiration tube of the tube fixed in the trachea, with the pressure inside the trachea being determined through the pressure measuring cannula and evaluated for purposes of controlling the respirator.

Further advantageous features are covered by the dependent claims.

Figure 2:
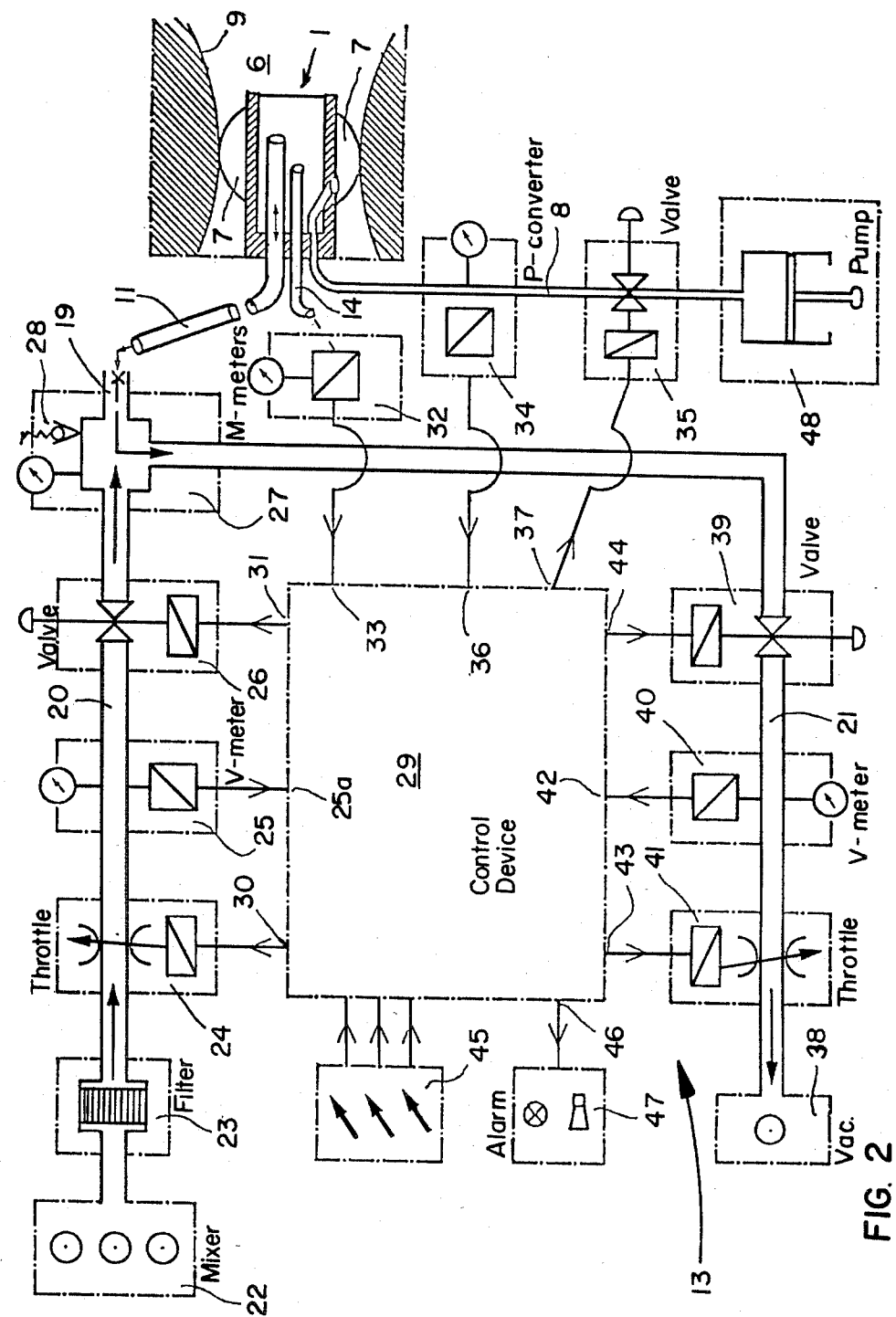

One embodiment of the invention is shown in the drawing in which:

FIG. 1 is a sectional view of an inventive tracheal tube, with a side view of the bundle of flexible tubes, and FIG. 2 is a block diagram of the respirator to be connected to the tracheal tube according to FIG. 1.

The tracheal tube 1 shown in FIG. 1 and introduced for respiratory purposes into the subglottic part of the trachea of a patient, comprises, in the present example, substantially a tube portion 2 having a diameter of about 7 mm and a length of about 7 cm. On its end 3 to be introduced, tracheal tube 1 has an opening 4 through which the inner space 5 communicates with the trachea 6 which is shown diagrammatically in FIG. 2. The central zone of tube portion 2 is surrounded by a balloon cuff 7 which can be inflated through an inflating cannula 8 until it applies against the wall 9 of the trachea, whereupon the tracheal tube 1 thus fixed forms with the lungs and with respirator 13 a closed respiratory system. For this purpose, inner space 5 of tube portion 2 is closed relative to the trachea 6 at a distal end 10.

A respiration tube 11 projects into inner space 5 of tracheal tube 1. At the distal end 10 of tube portion 2, the wall of respiration tube 11 is welded or other properly connected to the tube portion, to form a tight seal. Through respiration tube 11, the air needed for the ventilation is blown in or taken out by suction. The respiration tube 11 has a diameter of only a few millimeters, for example an inside diameter of three millimeters wherefore it produces a correspondingly high resistance to flow resulting in a considerable pressure drop.

Respiration tube 11 which may have a length of 40 cm, for example, is provided on its distal end with an adapter 12 for connecting to the respirator 13 shown in FIG. 2. To determine the pressure drop at respiration tube 11 and the intratracheal pressure, a pressure measuring cannula 14 is provided which is equipped with a connection 15. The proximal end of the pressure measuring cannula projects, as does respiration tube 11, into inner space 5 of tracheal tube 1, and is also welded in at distal end 10. The orifice 16 of pressure measuring cannula 14 is offset, relative to the orifice 17 of respirating tube 11, toward the distal end 10. Therefore, orifice 16 is located off the actual zone of flow in inner space 5 of tracheal tube 1, which makes the measuring of the pressure more accurate.

Within tube portion 2, inflating cannula 8 extends alongside the surface thereof while outside tube portion 2, cannula 8 is united by welding to respiration tube 11 and pressure measuring cannula 14, to form a flexible bundle of tubes which may have an approximately triangular cross section. As may be learned from the figure, connecting cannula 8 is provided in addition with a check balloon 18.

The tracheal tube 1 depicted in FIG. 1 is intended for being connected to a respirator which is shown in FIG. 2 and generally designated 13. Tracheal tube 1 and the subglottic part of the trachea 6 of a patient are diagrammatically indicated, with the opening 4 or free lumen of tracheal tube 1 being turned to the lungs of the patient. As shown in the drawing, balloon cuff 7 is inflated to such an extent that it applies against the wall 9 of the trachea, thereby insuring that the respiratory system is closed.

Respiration tube 11 is connected to the outlet 19 of the respirator, through which breathing air can be forced into respiration tube 11 or exhausted therefrom. For this purpose, respirator 13 comprises an excess pressure branch 20 and an underpressure branch 21. Excess pressure branch 20 is connected through an anesthetic gas mixer 22 to the central gas supply which is held under a pressure of about 6 bar. In the anesthetic gas mixer, the pressure is reduced to 2 bar. The breathing gas then passes through a foreign matter filter 23, a throttle valve 24 for the inspiration, a volumometer 25, and a selectively magnetically or manually controlled shutoff valve 26, to respirator outlet 19.

A manometer 27 indicates the pressure at respirator outlet 19, which is an excess pressure during the inspiration and an underpressure during the expiration. A safety valve 28 is also connected to respirator outlet 19.

During the inspiration of the patient, shutoff valve 26 is open, so that a breathing gas amount measurable with volumometer 25 is supplied through throttle valve 24 into respiration tube 11 and thus into the patient's lungs. To control the gas flow, a preferably electronically operating control device 29 is provided. During the inspiration, control device 29 delivers through outputs 30 and 31 suitable control signals to throttle valve 24 and shutoff valve 26. At the same time, the intratracheal pressure is determined through pressure measuring cannula 14 and the tracheal pressure measuring manometer 32, and converted into a suitable electric input signal for input 33 of control device 29. Another input supplied to control device 29 through input 25a during the patient's inspiration is a signal produced by volumometer 25.

In addition to tracheal pressure measuring manometer, a redundant pressure measuring system is provided comprising a manometer and a pressure converter 34 differentiating, on the one hand, the static air pressure in balloon cuff 7, and on the other hand, the breathing pressure variations acting on balloon cuff 7, as differential pressure, and, upon a failure of manometer 32 measuring the tracheal pressure, operates on control device 29 to avoid reaching of an undue pressure region. Simultaneously, with the response of the pressure safety system, a shutoff valve 35 is opened and balloon cuff 7 is deflated, whereby dangerous excess pressure or under pressure in the respiratory system of the patient is prevented. Upon opening shutoff valve 35, respiration is maintained as with the open injection ventilation, i.e. expiration is effected passively by the patient himself. As shown in FIG. 2, pressure converter 34 is connected to the input 36 and shutoff valve 35 is connected to the output 37 of control device 29.

During the expiration, underpressure branch 21 is effective through which the breath air is taken off. Under pressure branch 21 communicates with the central vacuum unit 38 delivering a pressure of −0.8 bar. Upon opening shutoff valve 39 which is actuable magnetically or, in emergency, manually, the breath air taken off through respiration tube 11 passes through a volumometer 40 and a second throttle valve 41 to the connection of the central vacuum unit 38. During the expiration, the signal supplied to input 42 of control device 29 is evaluated and control signals are delivered through outputs 43 and 44 to throttle valve 41 and shutoff valve 39. During the artificial respiration given to the patient, shutoff valves 26 and 39 are alternately open with intervals therebetween, so that respiratory gas is alternately blown into or exhausted from the trachea. By means of pressure measuring cannula 14 and the signal applied to input 33 of control device 29, the pressure in the trachea 6 is monitored to ensure that unphysiological pressure regions are not reached. With a failure of the control device 29, an emergency respiration may be produced since shutoff valves 26 and 39 are also actuable manually.

The respective desired respiration pattern may programmed, by means of three setting members. What can be preselected are the frequency of respiration, the inspiratory respiration minutes-volume, and the amount of the positive end expiration pressure (PEEPmbar). Should the desired respiration pattern exceed the predetermined pressure and flow limits, or should a failure occur, an alarm 47 is actuated through an output 46, so that a warning signal is given.

Balloon cuff 7 is inflated in the normal manner, by means of an air pump 48 or a syringe. The pressure needed for sealing, depending on the diameter of the trachea, is indicated by the manometers and pressure converter 34. Upon pushing the button, the electrically or manually actuable shutoff valve 35 closes the inflating cannula 8 to produce a closed respiratory system for the patient.

Respirator 13 serves the automatic, monitored control of the anesthesia and respiration, in connection with tracheal tube 1. Due to the small cross-sectional area of the flexible bundle of tubes comprising respirator tube 11, inflating cannula 8, and pressure measuring cannula 14, tracheal tube 1 enables the surgeon performing the endolaryngeal microsurgery to have a satisfactory view and convenient working conditions. Also, during an extended period of respiration, due to the smaller cross sectional area of the bundle of tubes comprising respiration tube 11, pressure measuring cannula 14, and inflating cannula 8, damages to the larynx region can be avoided. By monitoring and controlling the amount of the respiratory gas, respirator 13 makes the anesthesia and respiration safe.

We claim:

1. A respirator for giving artificial respiration to a patient, particularly in endolaryngeal surgery, comprising a tracheal tube having an open distal end and a closed proximal end, a balloon cuff surrounding the tracheal tube adjacent its distal end which is to be introduced, to an inflating cannula connected to said cuff, and a respiration tube extending into said tracheal tube through its proximal end and which terminates in the tracheal tube adjacent the distal end for injection ventilation, said distal end being sealed about said respiration tube, a pressure measuring cannula (14) extending into the interior (5) of the tracheal tube (2), said tracheal tube being sealed about said pressure measuring cannula, and a control device connected to said respiration tube and said pressure measuring cannula and including means for producing an excess pressure during the inspiration phase and an underpressure during the expiration phase in said respiration tube of said tracheal tube, when fixed in said trachea, in response to intratracheal pressure being measurable through the pressure measuring cannula and evaluatable for purposes of controlling the respirator.

2. A respirator according to claim 1, characterized in that both in the excess pressure branch (20) and the underpressure branch (21) a throttle valve (24,41) a volumometer (25,40), and a shutoff valve (26,29) are provided, with all of them being individually connected to the control device (29).

3. A respirator according to claim 1, characterized in that a manometer (32) connected to the pressure measuring cannula (14) produces through a converter a control signal (33) for the control device (29).

4. A respirator according to claim 3, characterized in that for a redundant determination of the intratracheal pressure a manometer (34) is provided at the inflating cannula (8), which is connected to one of the control inputs (36) of the control device (29).

5. A respirator according to one of claims 1, characterized in that a shutoff valve (35) is provided in the line to the inflating cannula (8), by which, at certain disturbances and through the control device (29), the closed respiratory system can be switched into an open respiratory system.

6. A respirator according to one of claims 1, characterized in that an alarm (47) is provided which can be made effective by the control device (29) upon exceeding determined limit values.

7. A respirator according to claim 1 wherein the control device (29) comprises setting members (45) for the respiration frequency, the inspiratory respiration minutes-volume, and the amount of the PEEP(positive end expiration pressure).

8. A tracheal tube connection for giving artificial respiration to a patient, comprising a tracheal tube having an open distal end insertable into a patient's trachea and an opposite closed proximal end, a balloon cuff extending around and connected to the exterior of said tube adjacent said distal end, an inflation cannula connected into said cuff for inflating said cuff to seal the exterior of said tracheal tube with the person's trachea, a respiratory line having means for providing both positive inhalation pressure and negative exhalation pressure connected through said proximal end of said tube, said proximal end of said tracheal tube being sealed around said respiratory line, and a pressure measuring cannula extending into said tracheal tube, said tracheal tube being sealed about said pressure measuring cannula.

9. A tracheal tube according to claim 8, characterized in that said pressure measuring cannula extends into said tracheal tube through said proximal end and that the proximal end (10) of the tracheal tube (1,2) the respiration tube (11), the pressure measuring cannula (14), and the inflating cannula (8) are welded to each other in a sealing manner.

10. A tracheal tube according to claim 9, characterized in that the respiration tube (11), the pressure measuring cannula (14) and the inflating cannula (8) are welded to each other over a predetermined length, and form a flexible bundle of tubes.

11. A tracheal tube according to claim 10, characterized in that the diameter of the tracheal tube at the proximal end thereof is larger than the cross section of said bundle of tubes (8,11,14).

12. A tracheal tube according to claim 8, characterized in that the respiration tube (11) has an internal diameter of about 3 mm, and the pressure measuring cannula of abount 1 mm.

13. A tracheal tube according to claim 8, wherein the respiration tube (11) projects into the interior of the tracheal tube (1,2) farther than the pressure measuring cannula (14).

* * * * *